United States Patent [19]

Megahed

[11] 4,192,320
[45] Mar. 11, 1980

[54] ADAPTER FOR SYRINGE

[75] Inventor: Shenoda S. Megahed, Rutherford, N.J.

[73] Assignee: Becton, Dickinson and Company, East Rutherford, N.J.

[21] Appl. No.: 819,667

[22] Filed: Jul. 28, 1977

[51] Int. Cl.[2] .............................................. A61B 5/14
[52] U.S. Cl. .................................................. 128/764
[58] Field of Search .............. 128/2 F, DIG. 5, 272.3, 128/215, 218 R, 218 D, 218 DA

[56] References Cited

U.S. PATENT DOCUMENTS

| | | | |
|---|---|---|---|
| 2,594,621 | 4/1952 | Derrick | 128/DIG. 5 |
| 3,539,300 | 11/1970 | Stone | 128/DIG. 5 |
| 3,608,550 | 9/1971 | Stawski | 128/272.3 |
| 3,877,465 | 4/1975 | Miyake | 128/2 F |
| 3,930,492 | 1/1976 | Hatsuno et al. | 128/2 F |

FOREIGN PATENT DOCUMENTS 308148  6/1955  Switzerland ...................... 128/DIG. 5

*Primary Examiner*—John D. Yasko
*Attorney, Agent, or Firm*—Kane, Dalsimer, Kane, Sullivan & Kurucz

[57] ABSTRACT

An adapter for use in accommodating a syringe with a reduced diameter open ended tip for use with a blood collecting needle so as to facilitate coupling of the syringe and needle and collecting of a sample of blood through the needle into the syringe. The adapter includes an elastomeric, pierceable, self-sealing member having a head portion and a body portion extending from one side of the head portion. A recess is located in the body portion conforming with the shape of the reduced tip of a syringe and is adapted to be mounted on the tip and close the open end thereof. A guide is on the head portion to assist in guiding the needle into alignment with the open end of the tip so that when the needle pierces the head portion it will extend through the open end of the tip into communication with the interior of the syringe to permit collection of a blood sample therein. The self-sealing head portion is adapted to reseal and close the open end of the reduced tip after the needle is removed therefrom.

8 Claims, 6 Drawing Figures

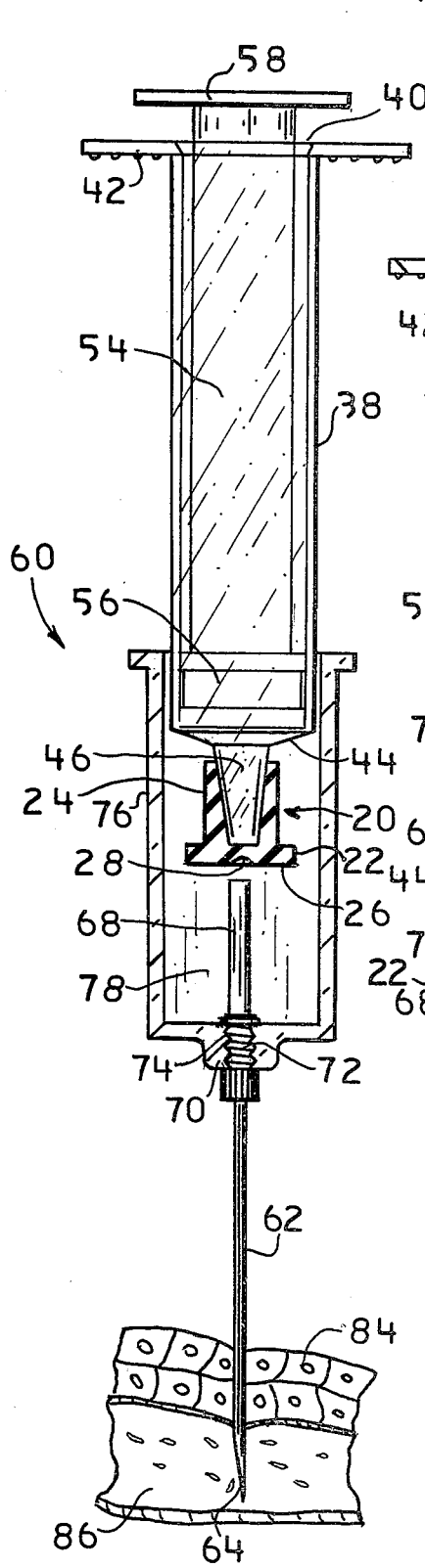
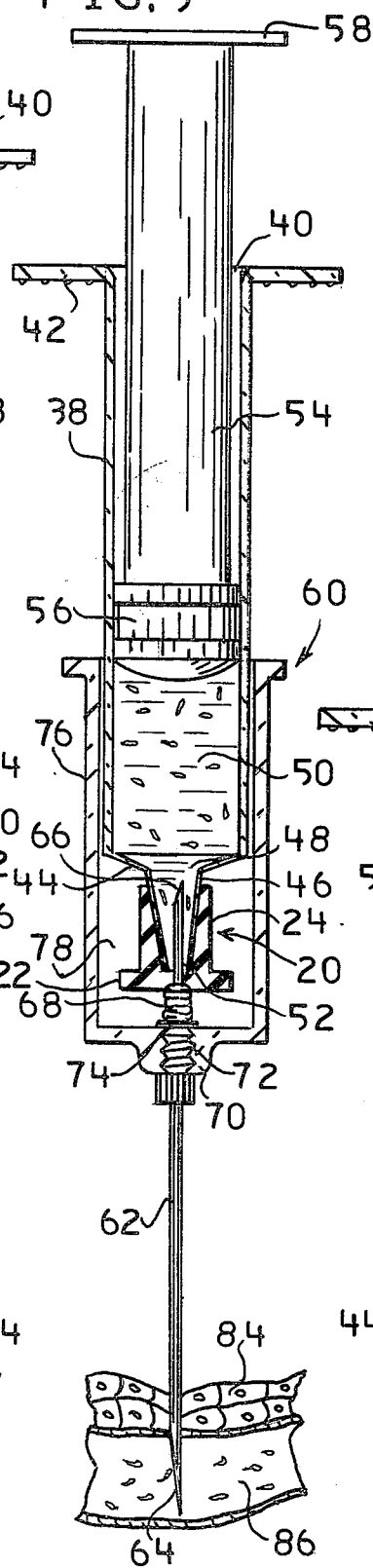
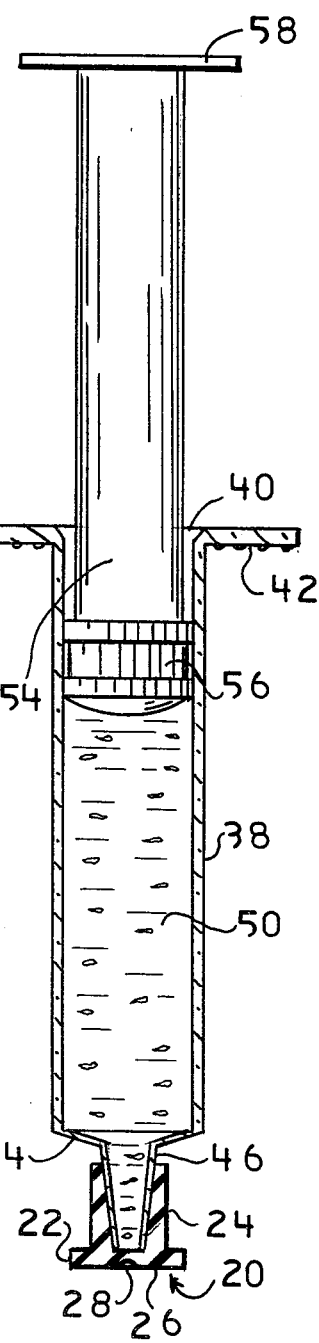

ADAPTER FOR SYRINGE

BACKGROUND OF THE INVENTION

Naturally in collecting blood samples, a double ended needle coupled with a holder is used. One end of the needle extends from the holder for entry to a vein and the other end extends into the holder where it is in position for introduction to a collection container. Blood samples are collected through the needle into a variety of different types of containers. For example, an evacuated, stoppered tube is commonly employed with the stopper being directed into the holder and into position so that the end of the needle within the holder pierces the stopper and communicates with the interior of the evacuated tube. The difference in pressure will then cause blood to flow through from the vein through the double ended needle and into the tube. The stoppered tube can then be removed from the needle whereupon the self-sealing stopper will seal the sample in the tube. The tubes are then used in a variety of different testing and clinical procedures.

For certain types of medical procedures, it is often desirable to collect the blood samples directly into containers which are different from the stoppered evacuated tube. This can be quite cumbersome, particularly when the container has an entranceway which is difficult to couple with the conventional double ended needle. An example of this type of container is a conventional syringe containing a reduced tip on the end which is to interconnect with the needle and a reciprocal plunger and stopper arrangement mounted in the syringe. The coupling between the syringe and needle must be done in a quick and efficient manner so that the blood flows directly into the syringe from the vein through the needle without blockage or leakage problems. Additionally, if the syringe is being used as the transportation container for the blood sample, it is often desirable to seal the open tip of the syringe after the sample has been collected so that the syringe containing the sample can be transported as a sealed unit for further use and testing procedures.

Accordingly, it would be extremely desirable to provide an adapter for a syringe of the above type which facilitates its coupling with the double ended blood collection needle assembly for collection of a blood sample and also provides a sealing means for the syringe when it is used as a storage container for the collected sample.

SUMMARY OF THE INVENTION

It is among the primary objectives of the present invention to provide an adapter of an elastomeric, self-sealing material which can be fitted on the reduced tip of a syringe to facilitate interconnection of the syringe with one end of a double ended needle for collection of a blood sample within the syringe and for operation as a seal or closure for the syringe tip with a sample contained within the syringe. The sampling process can be carried out quickly and efficiently without danger of leakage and without the necessity of modification to the conventional blood collecting needle assembly.

More specifically, the adapter of the present invention utilizes a guide means in the form of a cavity or dimple in the exposed surface of the adapter and in position to guide the needle through the adapter and through the reduced tip of the syringe into communication with the interior of the syringe when the syringe is coupled with the needle. Furthermore, the adapter acts as a closure for the syrine before and after collection of a sample to minimize contamination of the sample or the surrounding area. Also, if subsampling from the syringe is required in the later testing procedures, the adapter in the form of a closure is used as a cover. It is designed to be removed and replaced on the syringe tip in addition to its ability to be punctured thereby permitting exposure to the interior of the syringe in two ways. Furthermore, the adapter is designed to help the stability of the reduced tip syringe while a blood sample is being collected in view of the friction between the end of the double ended needle puncturing the adapter and the adapter material.

It is contemplated that the adapter can be formed of a conventional self-sealing, puncturable material such as natural or synthetic rubber or any conventional substitute therefor. It should also be noted that the adapter is designed for use with the conventional type of double ended needle with or without a sleeve closing the end of the needle to be introduced to the collection container.

The present adapter is designed to be positioned on very small reduced tip type syringe in that the adapter is mounted to the exterior surface of the reduced tip in contrast to being mounted interiorally thereof.

Also, the adapter of the present invention is particularly useful where a sample of blood is to be contained in a non-glass enclosure. The syringe can be formed of plastic or other materials without detracting from the operation of the system since interconnection between the needle assembly and the collection arrangement is accomplished by engaging surfaces of the cannula and the adapter. The needle assembly does not have to contact surfaces of the syringe.

In summary, an adapter is provided for use in accommodating a syringe with a reduced diamter open-ended tip for use with a blood collecting needle so as to facilitate coupling of the syringe and needle and collecting of a sample of blood through the needle into the syringe. The adapter includes an elastomeric, pierceable, self-sealing member having a head portion and a body portion extending from one side of the head portion. A recess is in the body portion conforming with the shape of the reduced tip of a syringe and adapted to be mounted on the tip and close the open end thereof. Guide means is on the head portion to assist in guiding the needle into alignment with the open end of the tip so that when the needle pierces the head portion it will extend through the open end of the tip into communication with the interior of the syringe to permit collection of a blood sample therein. The self-sealing head portion is adapted to reseal and close the open end of the reduced tip after the needle is removed therefrom.

With the above objectives among others in mind, reference is made to the attached drawings.

BRIEF DESCRIPTION OF THE DRAWINGS

In The Drawings:

FIG. 4 is a partially sectional plan view thereof with the syringe and adapter positioned in the holder prior to coupling with the needle assembly and with the needle assembly in the position of a successful venipuncture;

FIG. 5 is a partially sectional plan view thereof with the syringe assembly coupled to the needle assembly and blood being collected in the syringe;

FIG. 6 is a partially sectional plan view of the syringe and adapter with a collected blood sample in the syringe.

DETAILED DESCRIPTION

Figure 1:
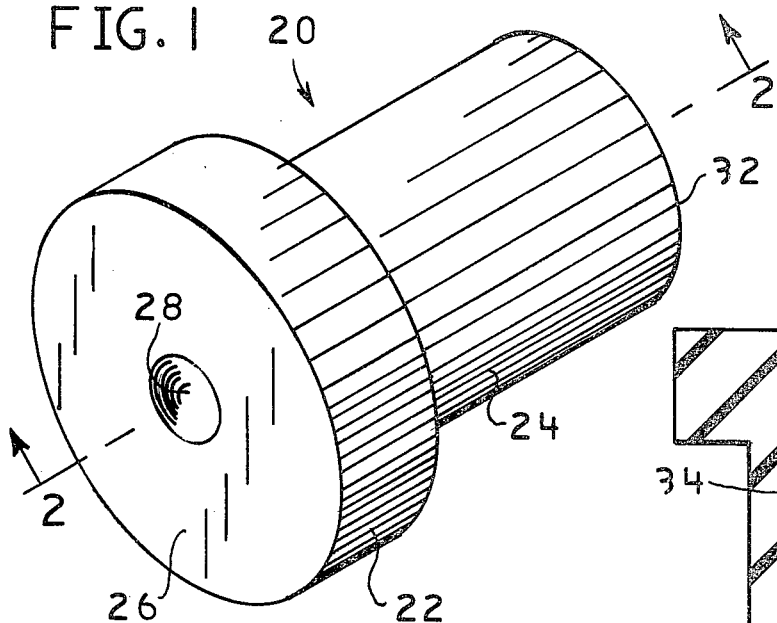
FIG. 1 is a perspective view of the adapter of the invention.
Figure 2:
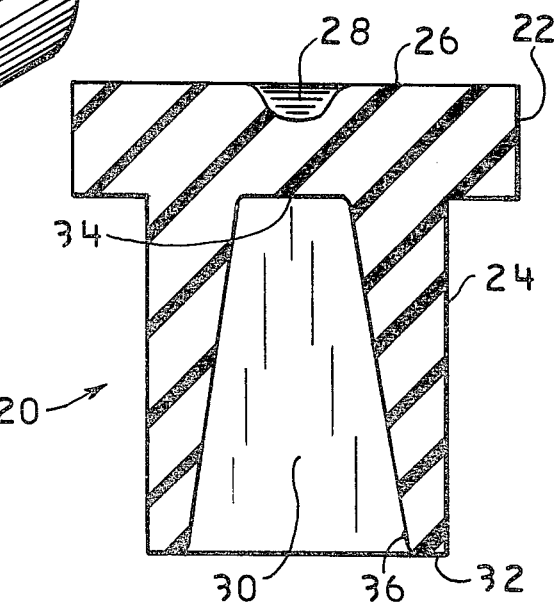
FIG. 2 is a sectional elevational view thereof.
Figure 3:
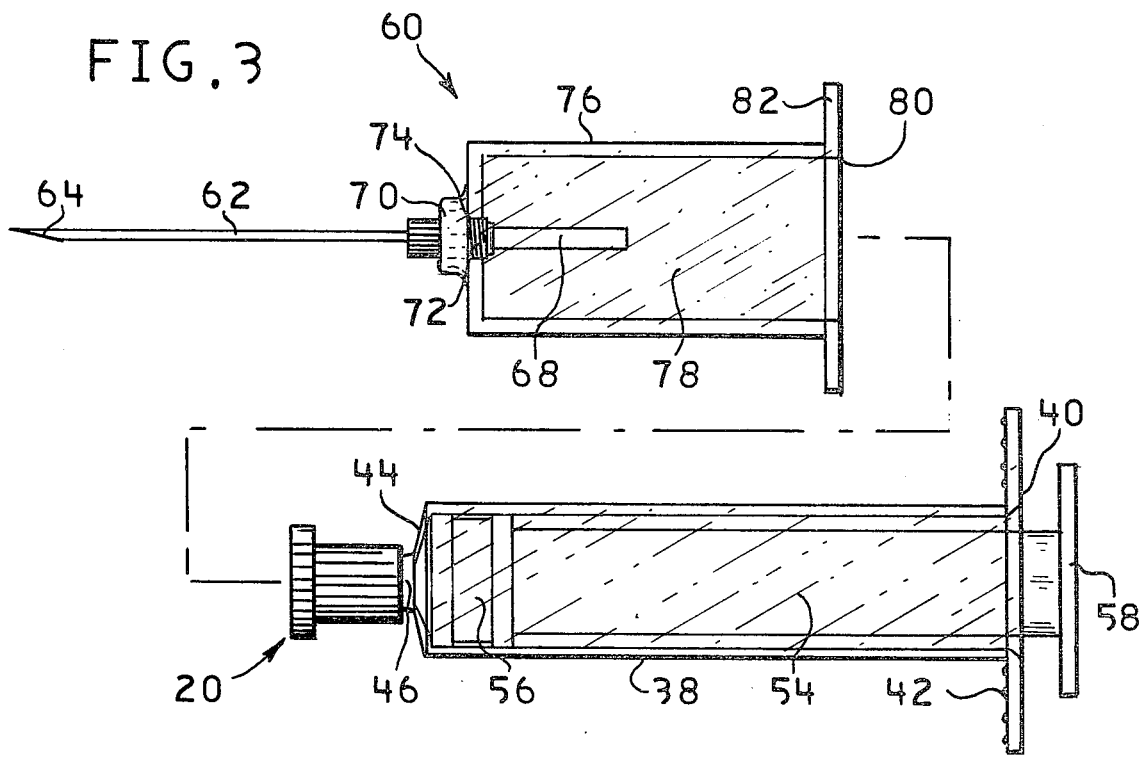
FIG. 3 is a plan view of a needle assembly and holder combination for blood collection and a syringe for collection of a blood sample with the adapter of the invention positioned thereon.

Adapter 20 is depicted in FIGS. 1 and 2. The adapter can be formed of a conventional elastomeric, self-sealing material such as natural or synthetic rubber or any conventional substitute therefor. Adapter 20 includes an enlarged head portion 22 and a body portion 24 extending therefrom and having a smaller outer diameter. The head portion 22 and the body portion 24 are integrally formed and are cylindrical in configuration. The exposed forward surface 26 of head portion 22 has a dimple or cavity 28 located therein which forms a guide means. A recess 30 is formed in the body portion 24 and is open at the end 32 of the body portion distal from the end attached to the head portion. The recess 30 is fustroconical in configuration tapering from a narrow diameter end wall 34 to a wider diameter rear edge 36. End wall 34 is axially aligned with dimple or cavity 28 so that a needle introduced through head 22 at the location of cavity 28 will directly communicate through end wall 34 of recess 30 and accordingly communicate with the interior of recess 30. The configuration of recess 30 permits its coupling with a reduced tip on a conventional syringe as shown in FIGS. 3-6. This type of syringe is one which has a cylindrical hollow barrel 38 with an opening 40 at the rear end and finger gripping flanges 42 extending therefrom. The forward end of barrel 38 has an inwardly tapering portion 44 terminating in a reduced diameter fustroconical tip 46. The tip 46 has a passageway 48 therethrough for communication with the interior 50 of barrel 38 and has an opening 52 at the end distal from the barrel. The fustroconical configuration of tip 46 is similar to the fustroconical configuration of recess 30 which is provided with a slightly smaller diameter so that the adapter 20 can be frictionally engaged with reduced tip 46. The frictional engagement permits the adapter to be removed with the application of sufficient force when desired.

A reciprocally movable plunger 54 is positioned in barrel 38 and the plunger 54 has a sealing stopper 56 on the forward end to seal with the side walls of the chamber 50 in syringe barrel 38. The rear end of plunger 54 has a finger gripping flange 58. Thus the operator can grasp the plunger rod and the syringe barrel with the help of finger gripping means 58 and 42 and reciprocally shift the plunger within the barrel. The syringe structure including the barrel 38, the plunger 54 and the plunger stopper 56 can be formed of conventional material such as glass, metal or plastic.

Adapter 20 is mounted on reduced tip 46 by frictionally sliding tip 46 into recess 30 until open end 52 of the tip is in engagement or adjacent to base wall 34 of the recess. In this manner, the adapter 20 forms a closure for the syringe. Chamber 50 is thus sealed by adapter 20 on one end and stopper 56 on the other end.

The syringe containing adapter 20 is used with a conventional blood collecting needle assembly 60 in collecting a blood sample from the vein of a patient directly into the chamber 50 in syringe barrel 38. The conventional type of needle assembly 60 includes a double ended cannula 62 with a pointed forward end 64 for performing a venipuncture and a pointed rear end 66 for piercing of the adapter 20 and providing communication between cannula end 64 and the interior chamber 50 in the syringe. In the relaxed position, a sleeve or cap 68 covers open rear end 66 of the needle preventing leakage therefrom. The sleeve is of a conventional type of elastomeric, self-sealing puncturable material, such as natural or synthetic rubber, which when collapsed will permit tip 66 to extend therethrough. When released, the elastomeric sleeve or cap 68 will return to the relaxed position and cover open end 66 once again sealing the end of the needle. Alternatively, as normally done in single sampling procedures, the needle assembly can be used without a sleeve.

Intermediate the ends of cannula 62 is a hub 70 mounted on the needle in a conventional manner, such as by use of epoxy. The hub has a threaded portion 72 adapted to threadedly interengage with a threaded aperture 74 of a holder 76. When the hub is mounted in the holder, the capped rear open end 66 of needle 62 is housed within chamber 78 of the hollow holder and the venipuncture end 64 extends from the holder. An opening 80 is in the rear end of the holder for introduction of the adapter 20 and coupled syringe therethrough. A flange 82 surrounds opening 80 to facilitate gripping of the holder when assembling the syringe and adapter with the holder.

In use, the adapter 20 is slipped on the tip of the syringe where it is frictionally held in place. As depicted in FIGS. 4-6, the syringe and coupled adapter 20 are introduced through open end 80 of the holder in alignment with the capped end 66 of needle 62. Venipuncture end 64 is then passed through the patient's tissue 84 and into the vein 86. Blood will not exit from open rear end 66 of the needle due to the closure provided by cap or sleeve 68. This condition is depicted in FIG. 4.

Then, as shown in FIG. 5, the adapter and coupled syringe are urged onto cannula 62 compressing sleeve 68 and permitting pointed end 66 to puncture the end of the sleeve and the head 22 of the adapter and enter the reduced tip 46 of the syringe. Collapsing of sleeve 68 is accomplished in a conventional manner with the sleeve being based against hub 70. By being based at one end, the sleeve can be biased and collapsed to expose open tip 66. Alignment for puncturing purposes is facilitated by the presence of dimple or cavity 28. The operator can align the covered end of the cannula 62 with the dimple 28 and be assured that the needle penetrating the head at that location will enter the tip into communication with chamber 50 in the syringe. As shown in FIG. 5, blood can then flow through the needle directly into the syringe. The blood flow is achieved by a combination of veneous pressure plus retraction of plunger 54 which aspirates the blood into chamber 50.

After the desired volume of sample has been collected in chamber 50, the syringe and coupled adapter can be removed from cannula 62 whereupon self-sealing elastomeric sleeve 68 will return to the relaxed position covering the rear open end 66 of cannula 62. No further blood can exit from the needle in this condition and the needle can be removed from the vein or retained in the vein and further samples collected in a similar manner in further collection containers.

The self-sealing elastomeric adapter 20 will seal once cannula 62 has been removed therefrom thereby forming a closure for open reduced tip 48 and sealing chamber 50 within the syringe. The chamber 50 is sealed on one end by adapter 20 and on the other end by the sealing engagement between stopper 56 and the inner walls of barrel 38. This sealed arrangement with the syringe acting as a container is depicted in FIG. 6. It can be used thereafter as desired for transportion, storage and testing purposes. Access can be gained to chamber 50 by piercing adapter 20 with a needle or similar structure or by removing the adapter with the application of sufficient force to overcome the frictional engagement between adapter 20 and reduced tip 46. In this manner, subsampling from the syringe can be carried out. Naturally, the adapter once removed can be repositioned to reclose the opening in reduced tip 46.

Cavity 28 on adapter 20 guides cannula 62 into alignment with syringe tip 46 and through the opening therein for communication with the interior of the syringe barrel. Adapter 20 acts as a closure for the syringe to minimize the danger of contamination of a collected sample or the surrounding area. If sub-sampling from the syringe is required, the adapter acting as a closure can be used as a cover and removed and replaced at will. Adapter 20 helps the stability of the syringe while blood is being collected due to the frictional between cannula 62 extending through adapter 20 and the self-sealing, elastomeric material of adapter 20. The only contact between the needle assembly 60 and the syringe assembly is through engagement with adapter 20. Thus, the remaining syringe structure can be formed of any desired material such as a metal, plastic or glass without having any material effect on the blood collection process.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

I claim:

1. A syringe assembly comprising: a syringe with a reduced diameter open-ended tip for use with a blood collecting needle so as to facilitate coupling of the syringe and needle and collecting of a sample of blood through the needle into the syringe, an adapter including an elastomeric, pierceable, self-sealing member having a head portion and a body portion extending from one side of the head portion, a recess in the body portion conforming with the shape of the reduced tip of the syringe and adapted to be removably mounted on the tip and close the open end thereof, the recess having a slightly smaller diameter in relaxed condition than the reduced tip of the syringe along their conforming interengaging surfaces thereby facilitating frictional interengagement therebetween and mounting of the adapter on the syringe and to provide for removal of the adapter to permit subsampling from the syringe to be carried out, guide means on the head portion to assist in guiding the needle into alignment with the open end of the tip so that when the needle pierces the head portion it will extend through the open end of the tip into communication with the interior of the syringe to permit collection of a blood sample therein, the self-sealing head portion adapted to reseal and remain mounted on the syringe and close the open end of the reduced tip after the needle is removed therefrom, the needle being in the form of a double ended hollow cannula with one end adapted for venipuncture and the other end adapted for puncturing the adapter and communicating with the interior of the syringe, a hub mounted intermediate the ends of the double ended cannula and having means thereon for mounting the hub to one end of a hollow holder with the end of the cannula to be introduced to the syringe extending into the holder and the end for venipuncture extending out of the holder, and the hollow holder being open at the end opposite to the end where the cannula is mounted to permit reciprocal introduction and removal of the syringe therein with the adapter mounted thereon for interengagement and removal from the cannula.

2. The invention in accordance with claim 1 wherein the end of the cannula extending into the hollow holder has a self-sealing elastomeric sleeve thereon normally covering the open end of the cannula within the holder and adapted to be compressed to cause the cannula to pierce the sleeve exposing the open end of the cannula within the holder, and when the sleeve is released, it will return to the relaxed position covering the end of the cannula within the holder.

3. The invention in accordance with claim 1 wherein the syringe tip has a fustroconical outer configuration tapering inwardly toward the open end thereof, the recess in the body portion of the adapter having a similar fustroconical configuration tapering outwardly toward the opening to the recess, the recess being dimensioned so that when the adapter is positioned on the reduced tip of the syringe the elastomeric adapter will frictionally engage with the tip and hold in fixed position thereon.

4. The invention in accordance with claim 1 wherein the reduced tip of the syringe has a passageway therethrough and extends from a larger diameter hollow barrel portion with the opening in the tip being open to the barrel portion of the syringe, the barrel of the syringe having an open end opposite to the reduced tip end, a reciprocally movable plunger in the barrel of the syringe, a sealing stopper on the end of the plunger movable with the plunger and to seal with the side walls of the barrel so as to form a chamber between the end of the sealing stopper and the reduced tip of the syringe so that as the plunger is withdrawn blood can be drawn into the syringe barrel through the reduced tip.

5. The invention in accordance with claim 1 wherein the recess in the body portion of the adapter is fustroconical in configuration tapering outwardly in the direction away from the head portion.

6. The invention in accordance with claim 1 wherein the guide means includes a cavity in an exposed face of the head portion of the adapter and aligned with the recess and, accordingly, aligned with the opening in the reduced tip of the syringe mounted in the recess so that passage of the needle through the head at the location of the cavity will direct the needle into the opening in the reduced tip of the syringe and into communication with the interior of the syringe.

7. The invention in accordance with claim 1 wherein the head portion of the adapter is cylindrical in configuration and the body portion of the adapter is cylindrical in configuration and has a smaller outer diameter than the head portion.

8. The invention in accordance with claim 1 wherein the the adapter is formed of rubber and the syringe is formed of plastic.

* * * * *